United States Patent

Segawa et al.

[11] 4,011,874
[45] Mar. 15, 1977

[54] DORNO RAY TRANSMITTING SHEET

[75] Inventors: Masahiro Segawa, Iwaki; Mitsuo Onozuka, Yokohama; Ichiroh Ishibashi, Iwaki; Shinsuke Yoshikawa, Iwaki; Shigeru Saitoh, Iwaki, all of Japan

[73] Assignee: Kureha Kagaku Kogyo Kabushiki Kaisha, Tokyo, Japan

[22] Filed: June 17, 1974

[21] Appl. No.: 480,447

[30] Foreign Application Priority Data

June 16, 1973   Japan .............................. 48-67894

[52] U.S. Cl. .................................... 128/362; 350/1; 350/175 NG; 428/339; 428/338; 428/910; 428/918; 428/421; 428/422; 428/332; 128/372

[51] Int. Cl.² ...................... A61N 5/06; G02B 1/04; C08F 3/22

[58] Field of Search .............. 161/402, 189, 165, 1, 161/408, 409; 260/92.15; 350/175 NG, 1; 428/336, 332, 338, 339, 918, 910, 421, 422; 128/372, 362

[56] References Cited

UNITED STATES PATENTS

| | | | |
|---|---|---|---|
| 2,617,149 | 11/1952 | Rubin | 260/92.1 S |
| 2,954,349 | 9/1960 | Jenness | 350/1 |
| 3,081,208 | 3/1963 | Bottorf | 260/92.1 S |
| 3,379,606 | 4/1968 | Bratton | 161/189 |
| 3,812,342 | 5/1974 | Mc Namara, Jr. | 161/189 |
| 3,850,900 | 11/1974 | Segawa | 260/92.1 S |

*Primary Examiner*—Ellis P. Robinson
*Attorney, Agent, or Firm*—Sughrue, Rothwell, Mion, Zinn & Macpeak

[57] ABSTRACT

A melt-molded polyvinylidene fluoride or polymonochlorotrifluoroethylene sheet having a thickness of about 20 $\mu$ to 2 mm and a spherulite size of less than about 10 $\mu$, whereby the sheet transmits more than about 40% of the dorno rays in a wavelength region of about 2,800 to 3,300 A, and a sun room using as a light admitting plate a sheet or plate of the polyvinylidene fluoride or the polymonochlorotrifluoroethylene permitting transmission of the physiologically active rays in sunlight.

5 Claims, No Drawings

DORNO RAY TRANSMITTING SHEET

BACKGROUND OF THE INVENTION

1. Field of the Invention

This invention relates to a sheet having a thickness of about 20 $\mu$ to 2 mm and having a spherulite size controlled to less than about 10 $\mu$ which is prepared by melt-molding a polyvinylidene fluoride or polymonochlorotrifluoroethylene resin. The sheet according to the present invention is a sturdy radiation transmitting material which transmits more than about 40% of the so-called dorno rays in a wavelength region of about 2,800 to 3,300A and is useful as a light admitting plate for a sun-room to admit the physiologically active rays in sunlight.

2. Description of the Prior Art

Ultraviolet rays having a wavelength in the region of 2800 to 3300A contained in sun radiation, i.e., the so-called dorno rays, are well-known to have an important physiological effect to convert ergosterin into vitamin $D_2$ upon exposure to physiologically active rays in sunlight. When severe rachitis has occurred in many localities in the world, exposure to physiologically active rays in sunlight has hitherto been advocated by pediatricians since ultraviolet rays are very helpful for prevention and treatment of rachitis, and therefore, exposure to physiologically active rays in sunlight for therapeutic purposes has been used world-wide for babies and infants before the development of vitamin $D_2$ synthesis. However, in recent years, dairy products containing vitamin $D_2$ additives have become easily available and only administration of powdered milk or cod-liver oil containing a large quantity of vitamin $D_2$ to babies and infants as a health measure has been considered sufficient to prevent rachitis without exposure to physiologically active rays in sunlight.

However, irregular mass examination in agricultural districts and a mountainous areas where babies and infants are usually fed on mother's milk has revealed that there is a tendency for the requirement of vitamin $D_2$ to not be met. A noteworthy tendency which has been recently observed is that many babies and infants in overpopulated industrial cities, particularly those who are brought up by a dual-income family and who live in a small room in an apartment house suffer from a light rachitis condition. Further, it is reported that, as a recent abnormal phenomenon, babies and infants who are brought up in an airconditioned room frequently lack exposure to physiologically active rays in sunlight, even in summer, thereby resulting in an increase in rachitis patients which has not previously been considered to be a problem in the summer.

That is, rachitis problems which have previously been limited to small villages without health care programs, remote villages in high snowfall areas and agricultural areas and other areas during the winter season due to with reduced occurrence of ultraviolet rays, have now been occurring more generally throughout the country and over the entire year.

A requisite amount of vitamin $D_2$ for babies and infants is believed to be about 400 to 800 IU per day. Nevertheless, it is reported in various parts of the country that an erroneous administration of vitamin $D_2$ in a dose level higher than 10,000 IU per day for a prolonged period of time resulted in death due to hypervitaminosis and that an administration of vitamin $D_2$ in a dose level of 1,800 IU per day, which is close to the requisite amount, retarded the normal growth of babies and infants or caused an abnormal hypercalcemia. These facts prove that an excessive intake of vitamin $D_2$ at a dose level of more than 2,000 IU, even at a level of 1,500 IU, would be very dangerous for babies and infants. Hence, mothers, even physicians, have come to realize that the safety margin between the amount of vitamin $D_2$ which is effective and the amount of vitamin $D_2$ which is toxic is very narrow and that oral administration of vitamin $D_2$ as a health measure may be hazardous to human health.

Since glass, clothes and the like scarcely transmit ultraviolet rays, many mothers have the burden of directly exposing their baby's body to physiologically active rays in sunlight for more than 30 minutes in the winter at which time dorno rays are very weak. Therefore, many proposals have been made to provide a material which sufficiently transmits dorno rays to allow indoor exposure to physiologically active rays in sunlight.

The results of measurement of monthly or hourly changes in solar radiation show that the amount of ultraviolet rays is poor over the period of from October to February. Exposure to physiologically active rays in sunlight is therefore necessary particularly during this period of the year. As far as dorno rays which have a wavelength of 2,800 to 3,300A and exhibit a physiological effect are concerned, the results of measurement of hourly changes in solar radiation show that the amount of energy reaches its maximum at 11 a.m. and the amount of energy obtained at 10 a.m. and between noon and 1 p.m. fall to half of the maximum value. Further, the results show that the amounts of radiation energy at 9 a.m. and 2 p.m. are almost equal corresponding to about 1/3 of the maximum value at 11 a.m. Accordingly, on exposure to physiologically active rays in sunlight during the fall and winter when the ultraviolet rays supplied are weak, the effective time for exposure is from about 9 a.m. to 2 p.m. while dorno rays after 3 p.m. become very weak and have such a low amount of energy that any health benefit is non-existant.

When physiologically active rays in sunlight passes through a high molecular weight material, it is assumed that the amount of the energy passed therethrough is decreased to only about 40% of the total amount of energy. This means that the maximum energy amount during the day (at 11 a.m.) falls to the level obtained on direct exposure at 8 a.m. to 9 a.m. or after 3 p.m. and that one cannot expect any beneficial effect from exposure to physiologically active rays in sunlight. Naturally, dorno rays are not only necessary for humans but also for animals and plants.

High molecular weight materials which permit the transmission of more than about 40% of dorno rays include polyolefins such as polyethylene, polypropylene and the like. However, the mechanical properties of these conventional materials are degraded markedly upon exposure to physiologically active rays in sunlight for several months and also the percent transmission of wavelengths of about 2,800 to 3,000A is decreased greatly due to the formation of a carbonyl group or a hydroxyl group arising from the splitting of the polyolefins main chains. Therefore, these materials are not considered to be suitable as a construction material for permanent facilities used for a long period of time.

Although anti-oxidants are generally incorporated into polyolefins as additives for the purpose of preventing the deterioration observed on standing, all of these additives have a property of absorbing ultraviolet rays and therefore, polyolefin materials having an improved weather-resistance are not useful where transmission of ultraviolet light, particularly dorno rays, is desired.

Polyfluorocarbon resins and acrylic resins are also known as high molecular weight materials. However, polytetrafluoroethylene has a high molding temperature which renders impossible the preparation of a strong and uniform sheet which can transmit more than about 40% of dorno rays. Polyvinyl fluoride and polymethyl methacrylate resins are considered to have good weather-resistance. However, not only do the mechanical properties of these materials deteriorate upon exposure to physiologically active rays in sunlight for a long period of time but also the percent transmission of dorno rays when used for a prolonged time decreases as compared with polyvinylidene fluoride. Particularly, polymethylmethacrylate is considered to have an extremely excellent transparency but this transparency can only be observed with visible rays and this material absorbs rays having a wavelength of 2,800 to 3,000 A so that it is not useful where transparency to rays having a wavelength corresponding to dorno rays is desired.

Polyvinylidene fluoride or polymonochlorotrifluoroethylene has excellent weather-resistance and can be easily molded to prepare a uniform sheet. However, those resin sheets having a spherulite size larger than about 10 $\mu$ which are prepared from these materials in a usual manner do not possess sufficient mechanical properties to resist wind pressure and snow load when they are exposed to cold winds or used in a snowy area, although they do show about 60 to 80% transmission of dorno rays when they are sufficiently thin, for example, less than about 20 $\mu$. Therefore, these sheets are unsuitable for use as a light admitting plate of a sun-room. In addition, if the thickness of the sheet is greater than about 20 $\mu$, the percent transmission of dorno rays is drastically decreased.

Methods for molding thermoplastic resin sheets generally include the melt-extrusion method and the casting method using a solvent. In the casting method, it is difficult to remove a trace amount of the solvent remaining in the product and the percent transmission of dorno rays is greatly decreased due to even an extremely small amount of the remaining solvent.

SUMMARY OF THE INVENTION

As a result of various investigations on factors which prevent polyvinylidene fluoride and polymonochlorotrifluoroethylene from transmitting ultraviolet rays, particularly in a wavelength region of about 2,800 to 3,300 A, a discovery has been made which cannot be explained by the conventional Beer's Law existing between the percent transmission and film thickness. That is, it has been found that the dependency of percent transmission of dorno rays on film thickness is small and materials having a transmission greater than 40% can be obtained when the spherulite size of polyvinylidene fluoride or polymonochlorotrifluoroethylene is less than about 10 $\mu$, preferably less than several microns with a sheet thickness ranging from about 20 $\mu$ to 2 mm.

DETAILED DESCRIPTION OF THE INVENTION

A suitable resin which can be used is a polyvinylidene fluoride resin and a polymonochlorotrifuoroethylene resin having an inherent viscosity, $[\eta]_{inh}$, ranging from about 0.8 to 1.8. The inherent viscosity of the resin is calculated by the following equation:

$$\eta_{inh} = [\ln \eta_r]/C$$

In the above equation $\eta_r$ stands for the relative viscosity and is measured at 30° C in dimethylformamide solution at a resin concentration of 0.4 g/100 cc. The relative viscosity $\eta_r$ means the viscosity ratio between the resin solution and the dimethylformamide as a solvent, and $[\ln \eta_r]$ represents a natural logarithm corresponding thereto. C denotes the weight of the resin in 100 cc of dimethylformamide. The polyvinylidene fluoride resin and the polymonochlorotrifluoroethylene resin which can be used in the present invention includes those prepared by a mass polymerization techniques, for example, as disclosed in U.S. Pat. No. 2,435,357, emulsion polymerization techniques, for example, as disclosed in U.S. Pat. No. 3,193,537, suspension polymerization techniques, for example, as disclosed in British Pat. Nos. 1,079,108 and 1,094,558 as well as other conventional procedures, and has a $\eta_{inh}$ of 0.8 to 1.8, preferably $\eta_{inh}$ of 0.9 to 1.5. If the viscosity $\eta_{inh}$ is lower than 0.8, the extrusion of the resin can easily be performed due to its low viscosity, but the crystallization tends to occur during the cooling. If the viscosity $\eta_{inh}$ exceeds over 1.8, the extrusion of the resin becomes difficult.

It has been found that when a film-shaped material obtained by the melt-extrusion of a polyvinylidene fluoride resin or a polymonochlorotrifluoroethylene resin is cooled and solidified by lowering the temperature of the film-shaped material to cool the film very rapidly the formation of large spherulites can be avoided.

One practical method for controlling the spherulite size to less than about 10 $\mu$, particularly, less than several microns, is a stretching method where a spontaneous flow orientation occurs at a die outlet were a melt-extruded resin has a temperature ranging from about 180° to 250° C and then heat-stretching is carried out up to about 1.8 times the spontaneous stretch magnification of the material simultaneously with growth of spherulites during a cooling step to about 160° to 180° C, the spherulite size is controlled to less than about 10 $\mu$. The "spontaneous stretch magnification" means the minimum stretch magnification required for completely eliminating the constriction produced in the stretched film during the stretching. The spontaneous stretch magnification varies depending upon the stretching conditions, the thickness of the film, and the type of resins, etc., and when a given film is stretched under given conditions the spontaneous stretch magnification is kept constant and is about 2 to 4 times. The spontaneous stretch magnification varies depending upon the stretching temperature and the thickness of the non-stretched film and, in general, falls within the range of 2.0 to 3.8 times at a thickness of 0.03 - 1.00 mm for a stretching temperature of 140° to 165° C.

Another method is a method in which a melt-extruded molding sheet extruded at about 180° to 250° C is cooled to a temperature from about 10° to about 50° C, preferably from 20° to 30° C, with the spherulites growing to about 10 to 100 $\mu$. With respect to this cooling step, below about 10° C no effect is observed in spherulite size while at a temperature above about 50° C, the film is too soft, and there is no tearing resistance.

Thereafter, the sheet is heated to a temperature of about 80° to 180° C, preferably 100° to 160° C, and then subjected to at least uniaxial stretching up to about 1.8 times the spontaneous stretch magnification to destroy those spherulites having a size greater than about 10 $\mu$ into fine crystals having a size less than about 10 $\mu$, particulary less than several microns. In practice, the latter method is employed because the rate of growth of polyvinylidene spherulites is quite high in the temperature range less than 150° C and the former method is very difficult to employ for production on an industrial scale. When stretching is sufficiently carried out by these methods as described above, the spherulites sometimes become so fine that detection of spherulite size is substantially impossible. The determination of the presence of spherulites and measurement of their size can be using a surface replica employing an electron microscope and by the observation employing a polarizing microscope.

An object of the present invention is, therefore, to provide a film or sheet of polyvinylidene fluoride or polymonochlorotrifluoroethylene having a thickness ranging from about 20 $\mu$ to 2 mm, preferably 50 $\mu$ to 1 mm, having spherulites of a size less than about 10 82, generally 0.1 to 10 $\mu$, preferably less than about 1 $\mu$, and being capable of the transmission of more than about 40% of dorno rays, which is useful as a light admitting plate for a sun-room in order to provide protection against weather and to admit dorno rays.

A sheet of polyvinylidene fluoride or polymonochlorotrifluoroethylene can be utilized as a roof or side wall of a sun-room even when the sheet has a thickness as high as 2 mm because of the excellent transmittance of dorno rays.

In such a sun-room, exposure to physiologically active rays in sunlight is possible while protection against the weather is obtained, and particularly, to let in dorno rays which are required for the production of vitamin $D_2$ in the human body even in winter. Such a sun-room can contribute to prevention and treatment of rachitis.

The polyvinylidene floride and polymonochlorotrifluoroethylene which can be used in the present invention include copolymers comprising polyvinylidene fluoride or polymonochlorotrifluoroethylene and about 1 to 30% by weight of at least one comonomer copolymerizable with vinylidene fluoride or monochlorotrifluoroethylene, such as ethylene, vinyl fluoride, tetrafluoroethylene, propylene hexafluoride and the like.

The invention is illustrusted in greater detail by reference to the following examples. Unless otherwise indicated, all parts, percents, ratios and the like are by weight.

EXAMPLE

A polyvinylidene fluoride resin having an inherent viscosity of 1.15 was melt-extruded at a temperature of 270° C and then cool-solidified on a roll heated at 120° C at a rate of 3 m per minute to prepare an unstretched film or sheet having a thickness of 50 $\mu$, 200 $\mu$ and 2 mm, respectively.

The rate of spontaneous stretch of the thus obtained sheet in a thickness of 2 mm was 2.6 times. The sheet was heated to 155° C and then stretched to 2.8 times in a longitudinal direction followed by stretching to greater than 3 times in a lateral direction thereby obtaining a biaxial-stretched film having a thickness of 50 $\mu$ and 200 $\mu$, respectively.

The properties of the films thus prepared were measured and the results obtained are shown in Table 1 below.

Table 1

| Sample | Thickness | Percent Transmission of Dorno Rays (%) | | | Spherulite Size* ($\mu$) |
|---|---|---|---|---|---|
| | | 2800A | 3000A | 3300A | |
| 1. Unstretched Film | 50 $\mu$ | 26 | 33 | 42 | 10 – 40 |
| 2. " | 200 $\mu$ | 16 | 20 | 28 | 10 – 60 |
| 3. " | 2 mm | 2 | 2 | 2 | 20 – 100 |
| 4. Biaxially Stretched Film | 50 $\mu$ | 75 | 78 | 80 | 0.1 – 3 |
| 5. " | 200 $\mu$ | 69 | 72 | 77 | 0.1 – 8 |

*The diameter of the spherulites was determined by observing a replica using an electron microscope and a polarization microscope.

Samples 4 and 5 in Table 1 above were prepared by biaxially stretching the unstretched sheet (Sample 3). From the results shown in Table 1, a marked difference in the percent transmission of dorno rays can be recognized when comparing these Samples 4 and 5 with the unstretched films having the same thickness (Samples 1 and 2). It was also confirmed that the destruction of spherulites occurred via a transformation of spherulites depending upon the size of spherulites.

The degree of deterioration in terms of weather-resistance was determined with respect to polyvinylidene fluoride and polymonochlorotrifluoroethylene of this invention using a weather-O-meter. The change in percent transmission of rays having a wavelength of 2,800A was monitored in a given period of radiation and the results obtained are shown in Table 2 below.

Table 2

| Sample | Thickness ($\mu$) | Period of Radiation (hrs.) | | | |
|---|---|---|---|---|---|
| | | 0 | 400 | 1000 | 4000 |
| 6. Polyvinylidene Fluoride | 50 | 80% | 77% | 75% | 72% |
| 7. Polymonochloro-Trifluoroethylene | 50 | 78% | 76% | 74% | 71% |
| 8. Polymethyl-methacrylate | 50 | 27% | 21% | 14% | 0% |
| 9. Polyvinyl Fluoride | 50 | 34% | 26% | 17% | 5% |

Note:
Sunshine Weather-O-meter WE SUN HC Type manufactured by Toyo Rika Co., Ltd. Japan was used.

While the invention has been described in detail and with reference to specific embodiments thereof, it will be apparent to one skilled in the art that various changes and modifications can be made therein without departing from the spirit and scope thereof.

What is claimed is:

1. A melt-molded polyvinylidene fluoride or polymonochlorotrifluoroethylene sheet having a thickness of about 20 μ to 2 mm and a spherulite size of between about 0.1 to 10 μ, whereby the sheet transmits between about 40% and about 80% of the dorno rays in a wavelength region of about 2,800 to 3,300A; said sheet having been formed by stretching in at least one axial direction a sheet formed from polyvinylidene fluoride or polymonochlorotrifluoroethylene resin having an inherent viscosity ranging from about 0.8 to 1.8.

2. The sheet of claim 1, wherein the spherulite size range is between 0.1 and 1 μ.

3. The sheet of claim 1, wherein said sheet comprises a melt-extruded sheet extruded at a temperature ranging from about 180° to 250° C followed by the cooling of the sheet to a temperature ranging from about 10° C to 50° C to permit spherulite growth to a size about 10 to 100 μ and subsequently heating at a temperature of about 80° to 180° C while at least uniaxially stretching the sheet.

4. A sun-room containing at least one light-admitting plate for admitting physiologically active rays in sunlight, said light-admitting plate comprising a plate of melt-molded polyvinylidene fluoride or polymonochlorotrifluoroethylene plate having a thickness of about 20 μ to 2 mm and a spherulite size of between about 0.1 to 10 μ, whereby the plate transmits between about 40% and about 80% of the dorno rays in a wavelength region of about 2,800 to 3,300 A; said plate having been formed by stretching in at least one axial direction a plate formed from polyvinylidene fluoride or polymonochlorotrifluoroethylene resin having an inherent viscosity ranging from about 0.8 to 1.8.

5. The sheet of claim 1, wherein said sheet has been biaxially stretched.

* * * * *